United States Patent
Chodkowski et al.

(10) Patent No.: US 12,128,186 B2
(45) Date of Patent: Oct. 29, 2024

(54) PATIENT INTERFACE VALVE ARRANGMENT

(71) Applicant: KONINKLIJKE PHILIPS N.V., Eindhoven (NL)

(72) Inventors: Lauren Patricia Chodkowski, Pittsburgh, PA (US); Daniel Steed, North Huntingdon, PA (US); Anna Dzuricky, Erie, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1193 days.

(21) Appl. No.: 16/444,730

(22) Filed: Jun. 18, 2019

(65) Prior Publication Data

US 2019/0388645 A1   Dec. 26, 2019

Related U.S. Application Data (60) Provisional application No. 62/688,643, filed on Jun. 22, 2018.

(51) Int. Cl.
*A61M 16/06* (2006.01)
*A61M 16/20* (2006.01)
*A61M 39/24* (2006.01)

(52) U.S. Cl.
CPC ......... *A61M 16/208* (2013.01); *A61M 16/06* (2013.01); *A61M 39/24* (2013.01); *A61M 2039/242* (2013.01); *A61M 2039/244* (2013.01); *A61M 2039/2493* (2013.01)

(58) Field of Classification Search
CPC ...... F16K 15/16; A61B 18/20; A61M 16/208; A61M 16/06; A61M 16/20; A41D 13/11–1192
See application file for complete search history.

(56) References Cited

U.S. PATENT DOCUMENTS

| | | | | |
|---|---|---|---|---|
| 4,414,973 A | * | 11/1983 | Matheson | A62B 18/00 128/206.17 |
| 5,331,957 A | * | 7/1994 | Liu | A62B 23/025 128/206.17 |
| 6,805,124 B2 | | 10/2004 | Japuntich | |
| 7,013,895 B2 | | 3/2006 | Martin | |
| 7,117,868 B1 | | 10/2006 | Japuntich | |
| 7,188,622 B2 | | 3/2007 | Martin | |

(Continued)

FOREIGN PATENT DOCUMENTS

| | | | | |
|---|---|---|---|---|
| EP | 1854494 A1 | 11/2007 | | |
| EP | 2196405 A1 | 6/2010 | | |
| GB | 825659 A | * | 11/1956 | ............. F16K 15/16 |

*Primary Examiner* — Courtney B Fredrickson
(74) *Attorney, Agent, or Firm* — Michael W. Haas (57) ABSTRACT

A valve arrangement includes a first member formed from a pliable material, the first member having at least one aperture defined therethrough. The valve arrangement also includes a second member coupled to the first member, the second member formed from another pliable material. The second member is movable from: a first position in which the second member is sealingly engaged about a periphery of the at least one aperture, thus preventing passage of a fluid through the aperture, and a second position in which at least a portion of the second member is spaced from the periphery of the aperture such that the fluid is able to pass through the aperture.

8 Claims, 8 Drawing Sheets

(56) References Cited

U.S. PATENT DOCUMENTS

| | | | |
|---|---|---|---|
| 7,493,900 B1 | 2/2009 | Japuntich | |
| 7,503,326 B2 | 3/2009 | Martin | |
| 8,757,156 B2 | 6/2014 | Martin | |
| 2004/0144435 A1 | 7/2004 | Dark | |
| 2009/0032019 A1* | 2/2009 | Green | A61M 15/0086 128/203.29 |
| 2009/0078264 A1 | 3/2009 | Martin | |
| 2009/0133700 A1* | 5/2009 | Martin | A62B 23/025 128/207.12 |
| 2010/0275909 A1* | 11/2010 | Anderson | A61M 15/0025 128/200.23 |
| 2013/0223979 A1* | 8/2013 | Locke | G01F 1/383 415/118 |
| 2014/0246025 A1* | 9/2014 | Cragg | A61M 16/0866 128/204.19 |

* cited by examiner

PATIENT INTERFACE VALVE ARRANGMENT

CROSS-REFERENCE TO RELATED APPLICATIONS

This patent application claims the priority benefit under 35 U.S.C. § 119(e) of U.S. Provisional Application No. 62/688,643, filed on Jun. 22, 2018, the contents of which are herein incorporated by reference.

BACKGROUND OF THE INVENTION

1. Field of the Invention

The present invention pertains to valve arrangements, and more particularly to vale arrangements for use in patient interface devices used in delivering a flow of breathing gas to the airway of a user.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

In order to ensure patient compliance, it is important to make such interface devices as comfortable and aesthetically pleasing as possible for the patient. Two common ways this has been attempted to be achieved is by minimizing the size of the mask on a patient's face and finding materials or combinations thereof which are of greater comfort on the face of a patient. In full face CPAP applications, such objectives are further complicated by the need for inclusion of an entrainment valve so that a patient does not suffocate in the event of an electrical or other failure of the system during treatment. Entrainment valves take up precious footprint space on the mask. Additionally, it is possible that the entrainment flapper may be incorrectly pushed through the valve, causing a mechanical malfunction. Even more, the entrainment valve often detracts from the overall aesthetics of the mask.

Accordingly, embodiments of the present concept provide improved valve arrangements which may be utilized as entrainment valves as well as patient interface devices which employ such valve arrangements.

SUMMARY OF THE INVENTION

Accordingly, it is an object of the present invention to provide improved valve arrangements which may be utilized as entrainment valves as well as patient interface devices which employ such valve arrangements.

As one aspect of the invention, a valve arrangement comprises: a first member formed from a pliable material, the first member having at least one aperture defined therethrough; and a second member coupled to the first member, the second member formed from another pliable material. The second member is movable from: a first position in which the second member is sealingly engaged about a periphery of the at least one aperture thus is structured to prevent passage of a fluid through the aperture, and a second position in which at least a portion of the second member is spaced from the periphery of the aperture such that the second member is structured to allow a fluid to pass through the aperture.

The second member may comprise a sheet-like pliable member.

The sheet-like pliable member may be of a generally constant thickness.

The at least one aperture may comprise a plurality of apertures; wherein when disposed in the first position, the second member may be sealingly engaged about a first periphery of a first aperture of the plurality of apertures and a second periphery of a second aperture of the plurality of apertures thus preventing passage of the fluid through the first aperture and the second aperture; and when disposed in the second position, at least a portion of the second member may be spaced from the first periphery of the first aperture and the second periphery of the second aperture such that the fluid is able to pass through the first aperture and the second aperture.

The at least one aperture may comprise a plurality of apertures, and the sheet-like pliable member may include: a first portion movable from a first position in which the first portion is sealingly engaged about a periphery of a first aperture of the plurality of apertures thus preventing passage of a fluid through the first aperture and a second position in which at least a portion of the first portion is spaced from the periphery of the first aperture such that the fluid is able to pass through the first aperture; and a second portion movable independently from a first position in which the second portion is sealingly engaged about a periphery of a second aperture of the plurality of apertures thus preventing passage of the fluid through the second aperture and a second position in which at least a portion of the second portion is spaced from the periphery of the second aperture such that the fluid is able to pass through the second. The first portion may be partially delineated from the remainder of the sheet-like pliable member by a first cutout provided in the sheet-like pliable member and the second portion may be partially delineated from the remainder of the sheet-like pliable member by a second cut-out in the sheet-like pliable member. The first cut-out and the second cut-out may be of a C-shape.

The sheet-like pliable material may have a thickness of about 0.001 inches.

As another aspect of the invention, a mask for use in a patient interface device for delivering a flow of breathing gas to the airway of a patient comprises: a first portion formed from a pliable material, the first portion having at least one aperture defined therethrough; a cavity defined at least in-part by the first portion, the cavity being structured to receive the flow of breathing gas and communicate the flow to the airway of the patient; and a member formed from another pliable material, the member disposed in the cavity and coupled to the first portion. The member is movable from: a first position in which the member is sealingly engaged about a periphery of the at least one aperture and is structured to prevent passage of the breathing gas from the cavity through the at least one aperture, and a second position in which at least a portion of the member is spaced from the periphery of the at least one aperture and is structured to allow passage of a gas external to the cavity into the cavity through the at least one aperture.

The member may comprise a sheet-like pliable member. The sheet-like pliable member may be of a generally constant thickness.

The at least one aperture may comprise a plurality of apertures; when disposed in the first position, the member may be sealingly engaged about a first periphery of a first aperture of the plurality of apertures and a second periphery of a second aperture of the plurality of apertures and is structured to prevent passage of the breathing gas through the first aperture and the second aperture; and when disposed in the second position, at least a portion of the member may be spaced from the first periphery of the first aperture and the second periphery of the second aperture and is structured to allow passage of a gas external to the cavity into the cavity through the first aperture and the second aperture.

The at least one aperture may comprise a plurality of apertures, and the sheet-like pliable member may include: a first portion movable from a first position in which the first portion is sealingly engaged about a periphery of a first aperture of the plurality of apertures thus preventing passage of a fluid through the first aperture and a second position in which at least a portion of the first portion is spaced from the periphery of the first aperture such that the fluid is able to pass through the first aperture; and a second portion movable independently from a first position in which the second portion is sealingly engaged about a periphery of a second aperture of the plurality of apertures thus preventing passage of the fluid through the second aperture and a second position in which at least a portion of the second portion is spaced from the periphery of the second aperture such that the fluid is able to pass through the second aperture. The first portion may be partially delineated from the remainder of the sheet-like pliable member by a first cutout provided in the sheet-like pliable member and the second portion may be partially delineated from the remainder of the sheet-like pliable member by a second cut-out in the sheet-like pliable member. The first cut-out and the second cut-out may be a C-shape. The sheet-like pliable material may have a thickness of about 0.001 inches.

The cavity may be readily deformable between a first positioning wherein the cavity defines a first volume and a second positioning wherein the cavity defines a second volume which is less than 60% of the first volume.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. As used herein, "selectively coupled" means that two components are coupled in a manner which allows for the components to be readily coupled or uncoupled in a predictable, repeatable manner without damaging either of the components. Unless particularly described otherwise herein, any components which are described merely as being "coupled", may also be "fixedly" or "selectively" coupled without varying from the scope of the present invention.

As used herein, the word "unitary" means a component is created as a single piece or unit. That is, a component that includes pieces that are created separately and then coupled together as a unit is not a "unitary" component or body. As used herein, the statement that two or more parts or components "engage" one another shall mean that the parts exert a force against one another either directly or through one or more intermediate parts or components. As used herein, the term "number" shall mean one or an integer greater than one (i.e., a plurality).

As used herein, the term "pliable" shall be used to refer to any material or combination of materials which are highly flexible and easily bent without having an adverse or negative effects on the material(s). Examples of pliable materials include, without limitation, silicone, thermoplastic elastomers, fabrics, coated fabrics, polyurethane, and other similar materials. In contrast, a rigid or semi rigid plastic (e.g., without limitation, thermoplastic polymers, such as polycarbonate) is not a pliable material as such term is used herein.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Embodiments of the present invention provide valve arrangements which may be utilized in applications where soft pliable materials are employed, where conventional valve arrangements would not work.

Figures 1A, 1B, 2A:
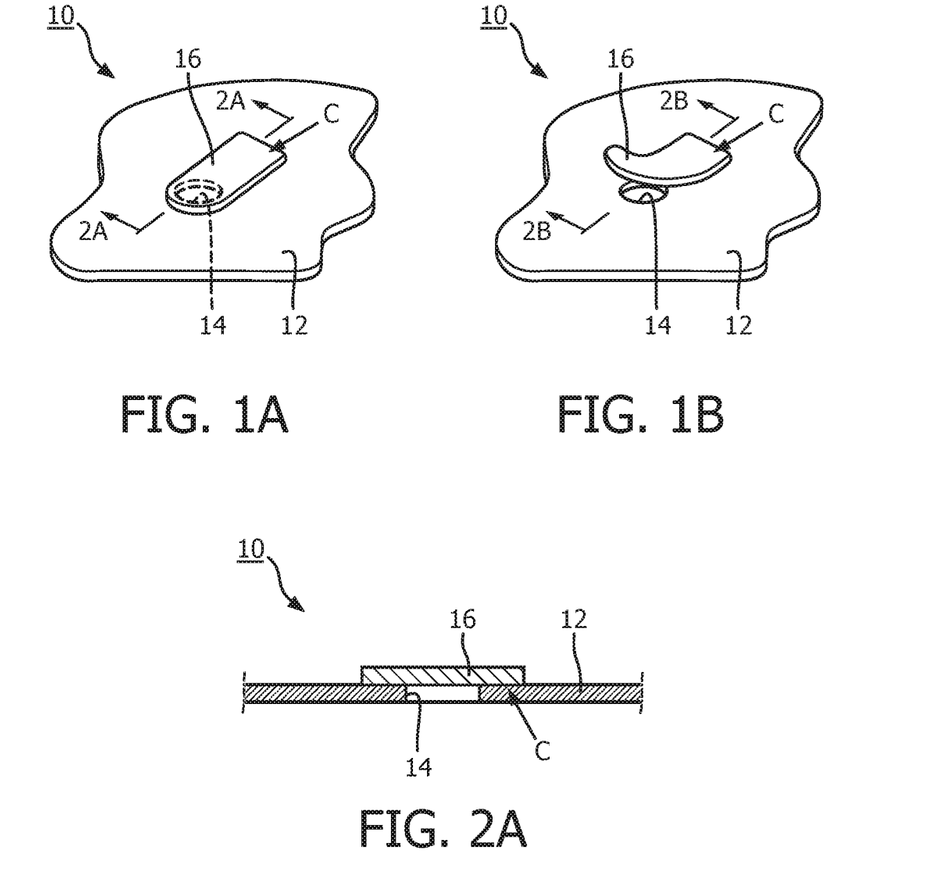
FIG. 1A is an isometric view of a valve arrangement in accordance with one example embodiment of the present invention shown in a closed position.
FIG. 1B is another isometric view of a the valve arrangement of FIG. 1A shown in an open position.
FIG. 2A is a sectional view of the valve arrangement of FIG. 1A taken along 2A-2A of FIG. 1A.
Figure 2B:
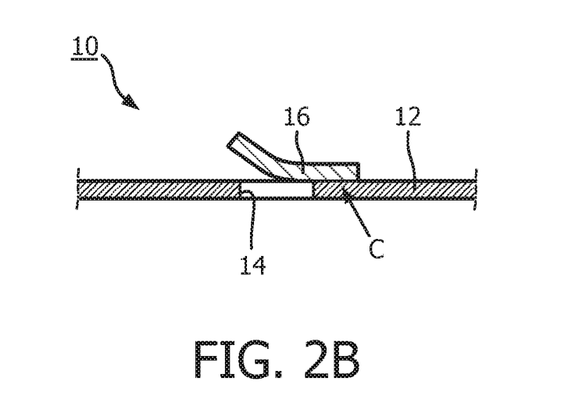
FIG. 2B is a sectional view of the valve arrangement of FIG. 1B taken along 2B-2B of FIG. 2A.
Figure 3A:
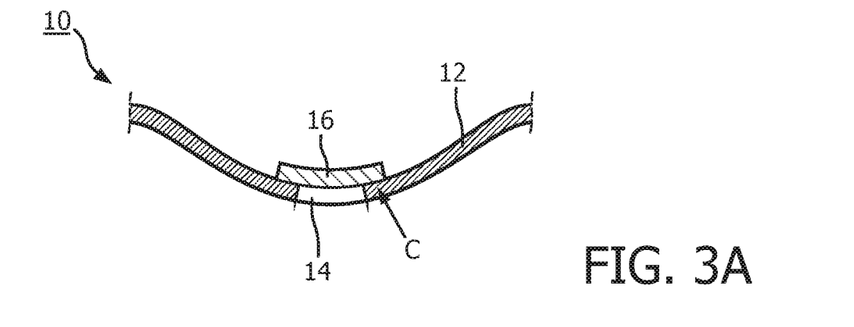
FIG. 3A is a sectional view of the valve arrangement of FIG. 1A, similar to FIG. 2A except that the valve arrangement is shown deformed in a concave manner.
Figure 3B:
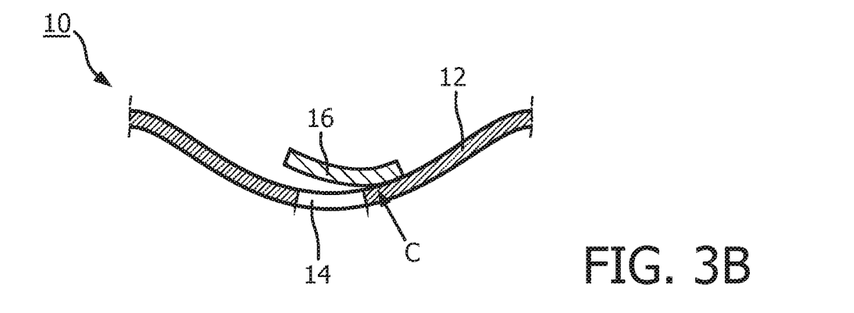
FIG. 3B is a sectional view of the valve arrangement of FIG. 1B, similar to FIG. 2B except that the valve arrangement is shown deformed in a concave manner.
Figure 4A:
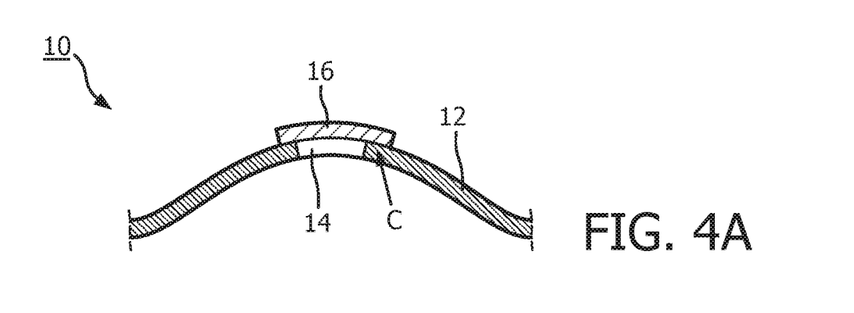
FIG. 4A is a sectional view of the valve arrangement of FIG. 1A, similar to FIG. 2A except that the valve arrangement is shown deformed in a convex manner.
Figure 4B:
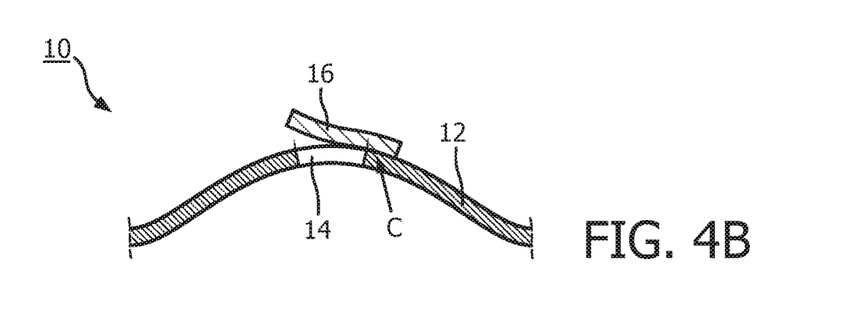
FIG. 4B is a sectional view of the valve arrangement of FIG. 1B, similar to FIG. 2B except that the valve arrangement is shown deformed in a convex manner.

Isometric views of a valve arrangement 10 in accordance with one example embodiment of the present invention shown respectively in closed and open positions shown in FIGS. 1A and 1B. Valve arrangement 10 includes a first member 12 (only a portion of which is shown in FIGS. 1A and 1B) formed from a pliable material. First member 12 includes at least one aperture 14 defined therethrough. Valve arrangement 10 further includes a second member 16 formed from another pliable material which is coupled to first member 12 in an area generally indicated C. Such coupling may be carried out via stitching, bonding, or any suitable means. Second member 16 is movable from a first position in which second member 16 is sealingly engaged about a periphery (not numbered) of aperture 14, such as shown in FIG. 1A, thus preventing passage of a fluid (e.g., a treatment gas) through the aperture and a second position, such as shown in FIG. 1B, in which at least a portion of second member 16 is spaced from the periphery of aperture 14 such that a fluid (e.g., environmental air) is able to pass through aperture 14. Such movement of second member 16 may readily be carried out by changing the air pressure on the side of first member 12 on which second member 16 is coupled. As will be discussed in further detail below, such change in air pressure may, for example, without limitation, be the result of the presence, or lack thereof, of a pressurized supply of a treatment gas.

In the example of FIGS. 1A and 1B, second member 16 is a sheet-like pliable member. In an example embodiment of the present invention a silicone sheet material having a thickness of about 0.001 inches was utilized. As a result of the pliability and thinness of second member 16, the need for a hinge-like structure (e.g., a groove or other localized thinning) is eliminated, hence second member 16 is of a generally constant thickness with variations in such thickness only a result of manufacturing tolerances.

By utilizing pliable materials for first and second members 12 and 16, valve arrangement 10 may be deformed in various ways while still maintaining desired functionality. FIGS. 2A, 2B, 3A, 3B, 4A and 4B show cross-sectional views of valve arrangement 10 distorted in various ways with second member 16 positioned in open and closed positions.

Figure 5:
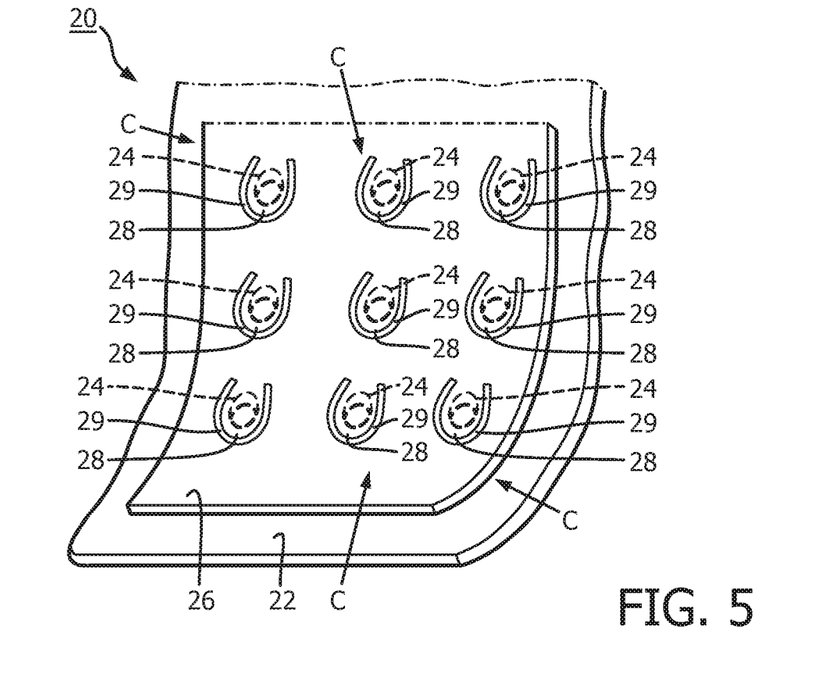
FIG. 5 is an isometric view of a valve arrangement in accordance with another example embodiment of the present invention.

Referring now to FIG. 5, an isometric view of a valve arrangement 20 in accordance with another example embodiment of the present invention is shown. Similar to valve arrangement 10, valve arrangement 20 includes a first member 22 formed from a pliable material and a second member 26 which is formed from another, sheet-like, pliable material which is coupled (in the area generally indicated C) to first member 22 via any suitable coupling means. Unlike first member 12 of valve arrangement 10 which only had one aperture 14 defined therein, first member 22 of valve arrangement 20 has a plurality (nine are shown in hidden line) of apertures 24 defined therein. Also, second member 26 of valve arrangement 20 includes a plurality of portions 28, each being partially delineated from the remainder of second member 26 by a cutout 29 provided in second member 26. In the example shown in FIG. 5, each cutout is formed generally as a C-shape, however it is to be appreciated that other shapes may be employed without varying from the scope of the present invention. Each portion 28 is movable from a first position in which each portion is sealingly engaged about a periphery (not numbered) of a respective one of the plurality of apertures 24, thus preventing passage of a fluid through apertures 24 (such as shown in FIG. 5), and a second position (not shown) in which at least a portion of each of portions 28 are spaced from the periphery of the respective apertures 24 such that the fluid is able to pass through apertures 24. It is thus to be appreciated that valve arrangement 20 generally provides an array of valves, each generally similar to that of valve arrangement 10.

Figure 6:
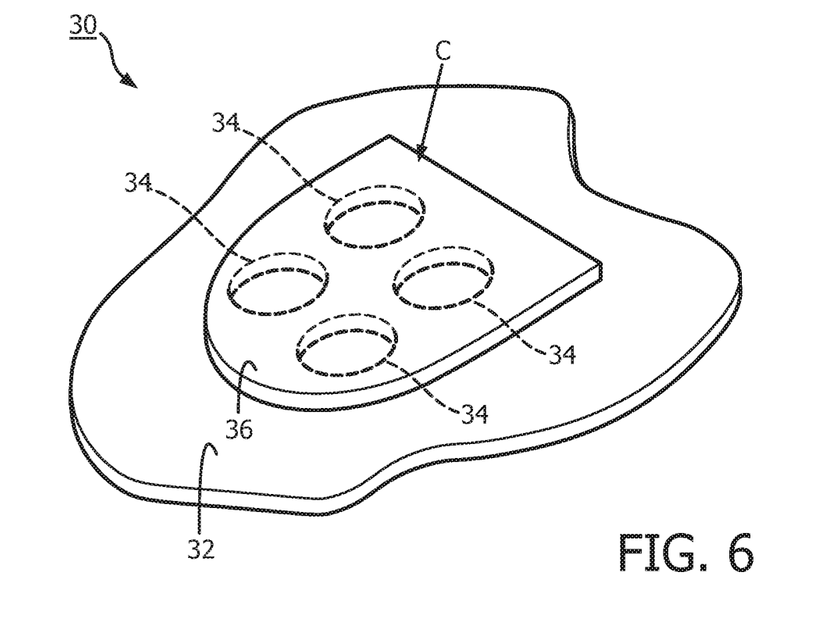
FIG. 6 is an isometric view of a valve arrangement in accordance with yet another example embodiment of the present invention.

Referring now to FIG. 6, an isometric view of a valve arrangement 30 in accordance with another example embodiment of the present invention is shown. Similar to valve arrangement 10, valve arrangement 30 includes a first member 32 formed from a pliable material and a second member 36 which is formed from another, sheet-like, pliable material which is coupled (in the area generally indicated C) to first member 32 via any suitable coupling means. Unlike first member 12 of valve arrangement 10 which only had one aperture 14 defined therein, first member 32 of valve arrangement 30 has a plurality (four are shown in hidden line) of apertures 34 defined therein. Like second member 16 of valve arrangement 10, second member 36 is movable from a first position (such as shown in FIG. 6) in which each second member 36 is sealingly engaged about the periphery (not numbered) of each aperture 34 of the plurality of apertures 34, thus preventing passage of a fluid through apertures 34, and a second position (not shown) in which at least a portion of second member 36 is spaced from the periphery of each of the respective apertures 34 such that the fluid is able to pass through apertures 34. It is thus to be appreciated that valve arrangement 30 provides an array of apertures with a single valve mechanism.

Having thus described the basic structure and operation of several valve arrangements 10, 20, 30 in accordance with example embodiments of the present invention, an example use of valve arrangements in accordance with the present invention as entrainment valves in a fabric or soft silicone mask/faceplate will now be described in conjunction with FIGS. 7-9.

Figure 7:
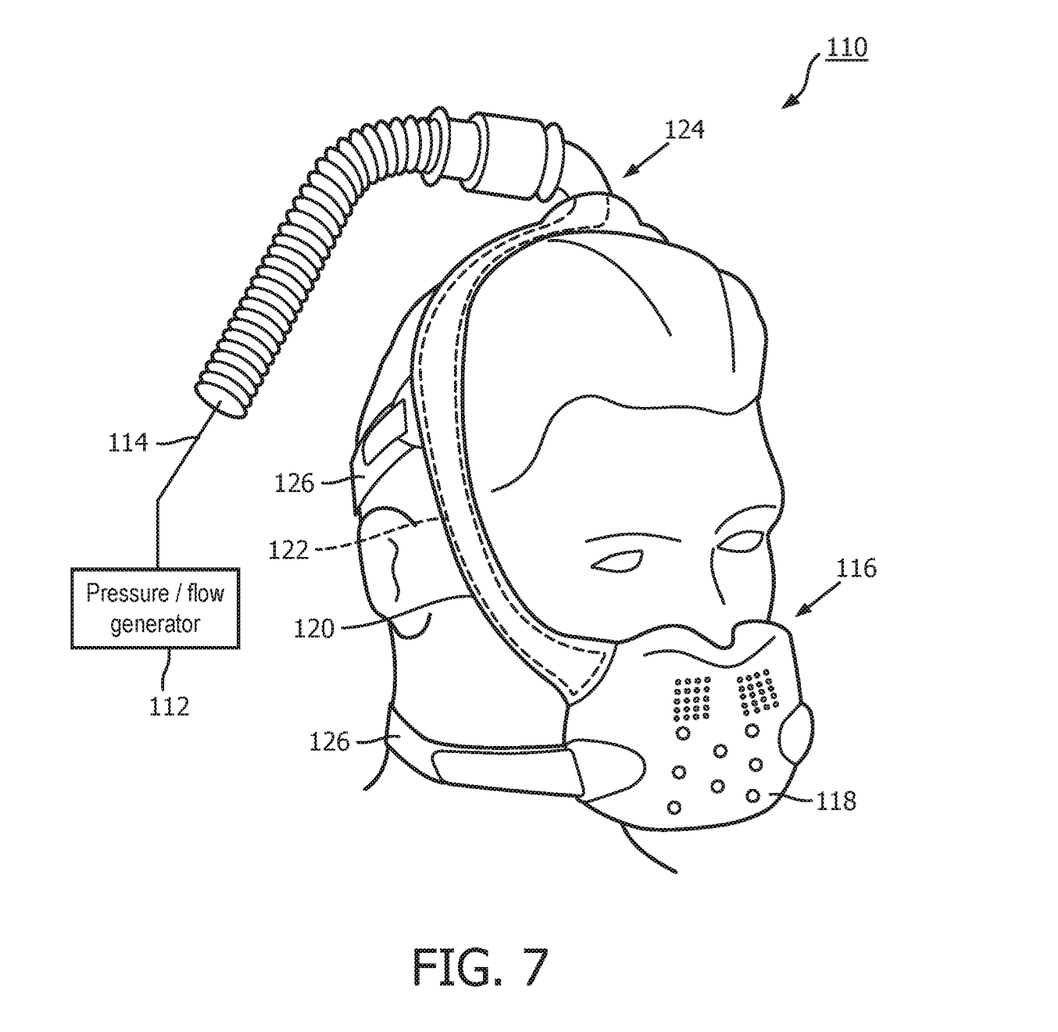
FIG. 7 is a partially schematic view of an airway pressure support system including a patient interface device in accordance with one example embodiment of the present invention shown disposed on the head of a user.

Referring first to FIG. 7, an example airway pressure support system 110 according to one particular, non-limiting exemplary embodiment of the present invention is shown. System 110 includes a pressure/flow generator 112 (shown schematically), a delivery conduit 114 (a portion of which is shown schematically), and a patient interface device 116 disposed on the head (not numbered) of a patient. Pressure/flow generator 112 is structured to generate a flow of breathing gas which may be heated and/or humidified. Pressure/flow generator 112 may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pennsylvania), and auto-titration pressure support devices. Delivery conduit 114 is structured to communicate the flow of breathing gas from pressure/flow generator 112 to patient interface device 116. Delivery conduit 114 and patient interface device 116 are often collectively referred to as a patient circuit.

A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. For present purposes, pressure/flow generator 112 is also referred to as either pressure generating device or gas flow generating device, because flow results when a pressure gradient is generated. The present invention contemplates that pressure/flow generator 112 is any conventional system for delivering a flow of gas to an airway of a patient or for elevating a pressure of gas at an airway of the patient, including the pressure support systems summarized above and non-invasive ventilation systems. Although described herein in example embodiments wherein a pressurized flow of gas is utilized, it is to be appreciated that embodiments of the invention as described herein could also be readily employed in other generally non-pressurized applications (e.g., without limitation, in high flow therapy applications).

In the exemplary embodiment of FIG. 7, patient interface device 116 includes a mask 118 which is structured to sealingly engage with the face of the patient about the mouth and nares of the patient. Patient interface device 116 further includes a frame 120 which is coupled to mask 118. Frame 120 includes an integrated gas pathway 122 (shown in hidden line) that carries the flow of breathing gas from an inlet 124, which is structured to be positioned at the top of a user's head, to mask 118. Patient interface device 116 further includes an adjustable headgear 126 for assisting in securing frame 120 and/or mask 118 to the head of a user.

Figure 8:
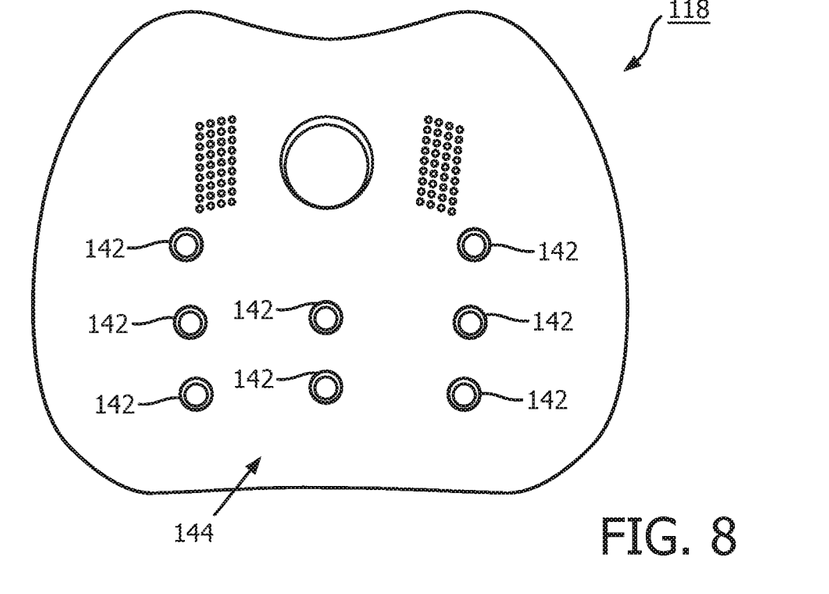
FIG. 8 is a front elevation view of the mask of the patient interface device of FIG. 7.
Figure 9:
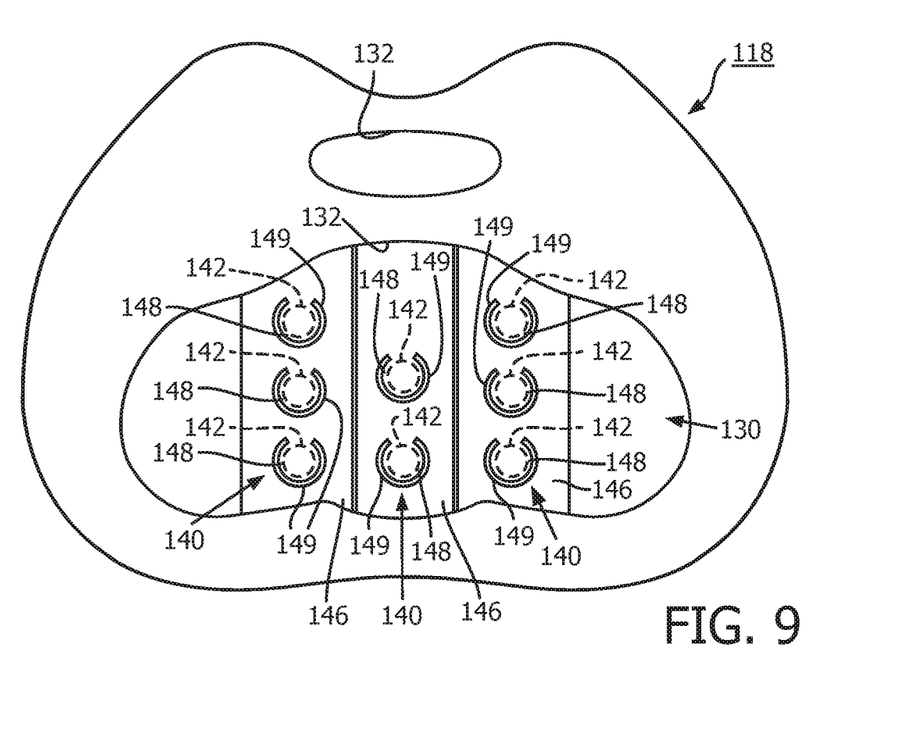
FIG. 9 is a rear elevation view of the mask of the patient interface device of FIG. 7.

Referring now to FIGS. 8 and 9 which generally show front and rear (patient facing) sides of mask 118, mask 118 is formed wholly, or in-part, from a generally, soft, pliable material (e.g., silicone, fabric, a silicone/fabric laminate, or other suitable pliable material), the benefits of such are discussed further below. Mask 118 includes a cavity 130 defined therein which is structured to receive the flow of breathing gas provided via gas pathway 122 of frame 120. Mask 118 further includes a number (two are shown in the example) of patient openings 132 through which the flow of breathing gas is provided from cavity 130 to the airway(s) of a user of mask 118 and a number exhaust port arrays 134 for exhausting exhalation gases of the patient from cavity 130.

As mask 118 covers both the mouth and nostrils of a user, mask 118 further utilizes a number of valve arrangements 140 which function as a number of entrainment valves, and which are of similar structure as valve arrangement 20 previously discussed in conjunction with FIG. 5. More particularly, as a part of such valve arrangements 140, mask 118 includes a number of apertures 142 (eight are shown in the example embodiment, similar to apertures 24 of FIG. 5) which are each defined in a portion (shown generally at 144 in FIG. 8, similar to first member 22 of FIG. 5) of mask 118 which is formed from the aforementioned soft, pliable material. Each aperture 142 provides a passage between cavity 130 and the surrounding environment outside of mask 118. As another part of such valve arrangements 140, each valve arrangement 140 includes a member 146 (similar to second member 26 of FIG. 5) formed from another pliable material (e.g., without limitation, silicone, thermoplastic elastomers, etc.), which is disposed in cavity 130 and coupled to portion 144 of mask 118. Each member 146 has a number of portions 148 (similar to portions 128 of FIG. 5) which correspond to the number of apertures 142 associated therewith. Each portion 148 is partially delineated from the remainder of member 146 by a respective cutout 149 (similar to cutouts 29 of FIG. 5) provided in each member 146. Each portion 148 of member 146 is movable from a first position (such as shown in FIG. 9) in which each portion 148 is sealingly engaged about a periphery (not numbered) of a respective aperture 142 in a manner such that each aperture 142 is blocked, and thus the flow of treatment gas is prohibited from escaping from cavity 130 via any of the number of apertures 142; and a second position in which at least a portion of each portion 148 is spaced from the periphery of the respective aperture 142 such that ambient air from outside of cavity 130 and mask 118 can enter cavity 130 via aperture 142 and thus be inhaled by a user of mask 118.

From the foregoing, it is to be appreciated that such first positioning of portions 148 would occur when the pressure inside cavity 130 is generally equal to or greater than the ambient pressure outside of cavity 130 and mask 118 such as when mask 118 is donned by a user and a supply of gas is provided to cavity 130 which is greater than that inhaled from cavity 130 by the user of mask 118. Conversely, such second positioning of portions 148 would occur when the pressure inside cavity 130 is less than the ambient pressure outside of cavity 130 and mask 118 such as when the mask is donned by a user and when an inadequate or no supply of gas is provided to cavity 130 to accommodate the amount of gas inhaled by the user from cavity 130. Accordingly, valve arrangements 140 function as multiple entrainment valves.

It is to be appreciated that by using generally soft, pliable materials, mask 118 provides for improved comfort over masks which utilize generally rigid components and also provides for an arrangement which can be readily condensed for travel. For example, mask 118 can be readily compacted (as well as readily de-compacted) from an in-use form when donned by a user in which cavity 130 is of a first volume to a much more compact second form for storage (e.g., for travel) in which cavity 130 is of a second volume which in some example embodiments is: less than 60% of the first volume, less than 50% of the first volume, and even less than 40% of the first volume.

It is also to be appreciated, that although shown with valve arrangements 140 similar to valve arrangement 20 previously discussed, other valve arrangements in accordance with the present invention (e.g., without limitation, valve arrangements 10 and 30 previously described) may be readily employed in addition to, or in place of valve arrangement 20 without varying from the scope of the present invention.

It is also to be appreciated that embodiments of the present invention also allow for valves to be provided in soft collapsible tubes. It is to be further appreciated that embodiments of the present invention provide enhanced breathing comfort when therapy is off as embodiments of the invention provide for entrainment features to be soft and near the mouth, which means direct fresh airflow when the pressure is not on.

As an alternative approach to the valve arrangements previously described herein, the present invention also contemplates other solutions for providing a user of a full face mask with access to ambient air in the event of a system failure. In such arrangements, during therapy the CPAP mask utilizes an (ideally) air-tight seal between the CPAP mask and the face of the user. The general concept of the alternative approach is to implement a shape change of all or of a selected portion or portions of the mask in a manner which purposefully breaks the CPAP mask seal. When the user is getting ready for bed and is strapping the CPAP mask to their face, the mask has a shape that does not create a perfect seal between the user and atmospheric air. When the CPAP blower is turned on and therapy is active, the mask inflates/morphs to a shape that seals. When the blower turns off, the mask again changes shape to a state where the seal is broken, allowing the patient to breathe atmospheric air.

Figure 10:
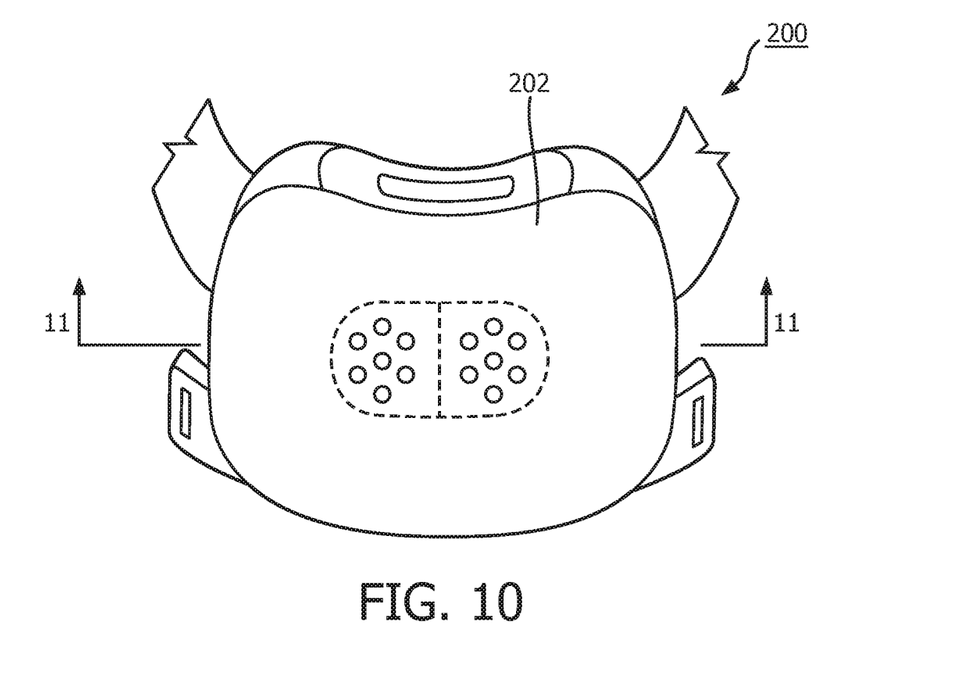
FIG. 10 is a front view of a mask in accordance with one example embodiment of the present invention.
Figure 11A:
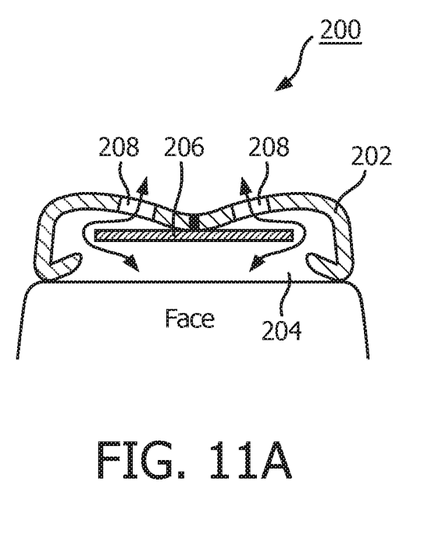
FIGS. 11A and 11B are sectional views of the mask of FIG. 10 taken along line 11-11 of FIG. 10 showing the mask positioned in first and second positionings.
Figure 11B:
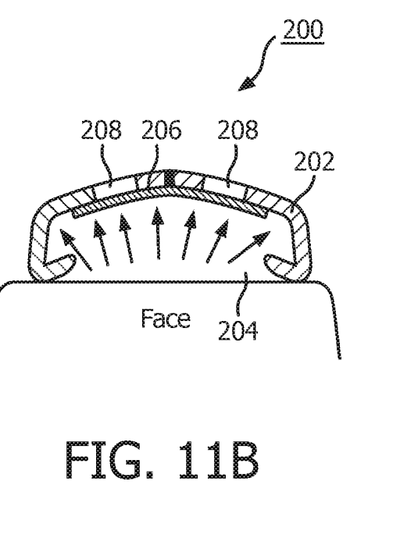

A mask 200 in accordance with an example embodiment of the present invention which utilizes the aforementioned approach is shown in FIGS. 10, 11A and 11B. Mask 200 includes a pliable housing 202 formed from a highly flexible silicone, fabric, or other similar material or materials which defines a cavity 204 therein for receiving a flow of treatment gas. Mask 200 further includes a generally rigid inner member 206 which is sized and configured to selectively seal against a number of apertures 208 which are defined in housing 202 and extend between cavity 204 and the ambient atmosphere. More particularly, such "selective sealing" by member 206 is provided as follows. As shown schematically in the sectional view of FIGS. 11A and 11B, housing 202 is structured to sealingly engage against a user's face such that the flow of treatment gas can be delivered from cavity 204 to the airways of a user.

When no flow or an insufficient flow (i.e., not enough to meet the inhalation requirements of the user) is provided to cavity 204, housing 202 is of a first shape, such as shown in FIG. 11A. In such first shape, housing 202 is distorted such that apertures 208 are spaced from inner member 206, thus allowing ambient air to pass into, and gases to readily exit, cavity 204, such as shown by the arrows in FIG. 11A. Conversely, when a sufficient flow of treatment gas is provided to cavity 204 housing 202 is transitioned into a second shape in which the inner end of apertures 208 are sealed against inner member 206, thus preventing the passage of ambient air into cavity 204. It is to be appreciated that although not shown in FIGS. 11A and 11B, in such example positionings mask 200 would be generally held on a user's face by a suitable headgear arrangement, which similarly applies to the similar views of further embodiments shown in FIGS. 13A, 13B, 14A, 14B, 15A, 15B, 16A and 16B discussed further below.

Figure 12A:
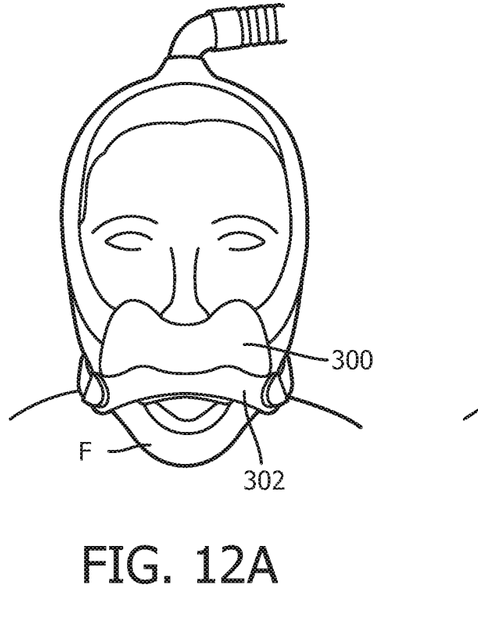
FIGS. 12A and 12B are front views of a patient interface device in accordance with one example embodiment of the present invention disposed on the head of a user shown with a mask thereof disposed in first and second positionings.
Figure 12B:
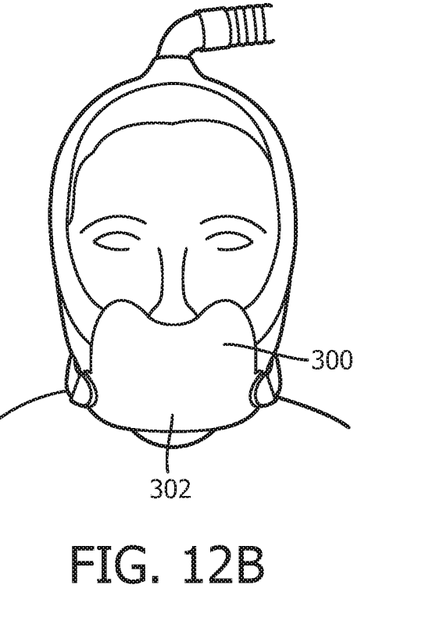

Another mask 300 in accordance with an example embodiment of the present invention which utilizes the aforementioned approach is shown in FIGS. 12A and 12B. Mask 300 utilizes a flexion point or hinge built in to the design. More particularly, as shown in FIG. 12A, when at rest (i.e., when no or an insufficient flow of treatment gas is provided) the hinge allows a portion 302 of mask 300 to deform away from the face F of the user, thus allowing the user to readily breath ambient air. Conversely, during therapy, the pressure of the air causes the mask to inflate, thus resulting on portion 302, as well as the remainder of mask 300, to seal against the face of the user, such as shown in FIG. 12B.

Figure 13A:
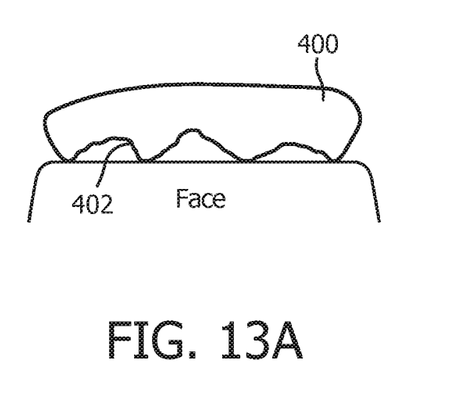
FIGS. 13A and 13B are schematic sectional views of a mask in accordance with one example embodiment of the present invention taken from a similar position as the sectional views of FIGS. 11A and 11B.
Figure 13B:
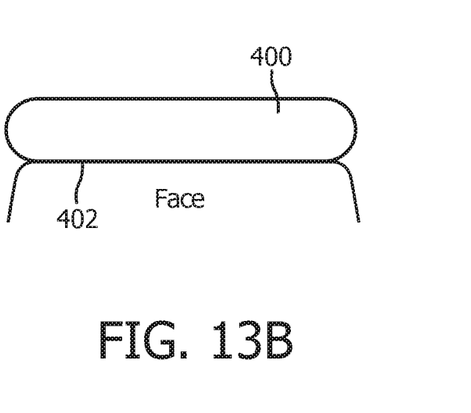

FIGS. 13A and 13B show schematic section views, similar to those of FIGS. 11A and 11B, of a mask 400 in accordance with an example embodiment of the present invention disposed on the face of a user. Referring to FIG. 13A, mask 400 includes a thin sealing flap 402 which, when no flow or an insufficient flow of treatment gas is provided, is structured to not contour to the skin of the face of a user, thus leaving air gaps, shown generally at 404, through which ambient air may readily pass to the user. Conversely, as shown in FIG. 13B, during therapy, the pressure of the flow of treatment gas causes a stretch and/or shape change which pushes sealing flap 402 into the face, thus preventing the passage of ambient air to the patient.

Figure 14A:
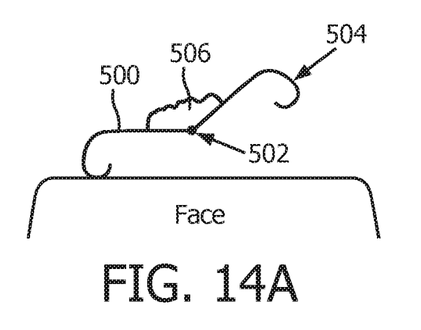
FIGS. 14A and 14B are schematic sectional views of a mask in accordance with one example embodiment of the present invention taken from a similar position as the sectional views of FIGS. 11A and 11B.
Figure 14B:
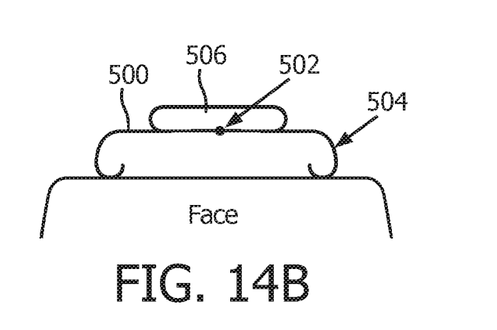

FIGS. 14A and 14B show schematic section views, similar to those of FIGS. 11A, 11B, 13A and 13B, of a mask 500 in accordance with an example embodiment of the present invention disposed on the face of a user. Referring to FIG. 14A, mask 500 includes a flexion point or hinge 502. When at rest, hinge 502 allows a portion, shown generally at 504, of mask 500 to pull away from the face of a user, thus allowing the user to readily breath ambient air. During therapy, an inflatable pouch 506 or other suitable structure provided as a part of mask 500 is inflated which pushes on portion 504 of mask 500, causing it to move towards the face and create a seal against the face of the user.

Figure 15A:
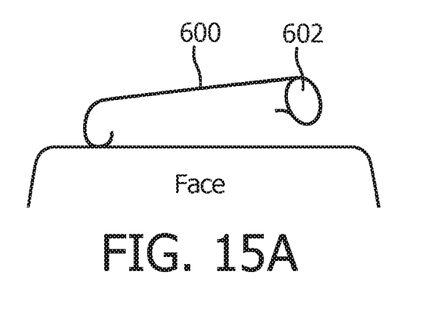
FIGS. 15A and 15B are schematic sectional views of a mask in accordance with one example embodiment of the present invention taken from a similar position as the sectional views of FIGS. 11A and 11B.
Figure 15B:
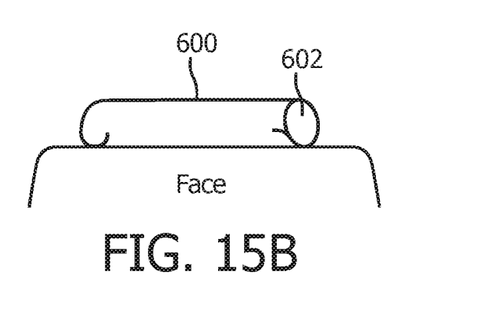

FIGS. 15A and 15B show schematic section views, similar to those of FIGS. 11A, 11B, 13A, 13B, 14A and 14B, of a mask 600 in accordance with an example embodiment of the present invention disposed on the face of a user. Referring to FIG. 15A, mask 600 includes an area with a number of thin-walled pouches 602 built into the sealing area which are deflated when no flow or an insufficient flow of treatment gas is provided, thus causing one or more air gaps, such as shown in FIG. 15A. Conversely, when a sufficient flow of treatment gas is provided, the number of pouches 602 inflate, thus causing mask 600 to tightly seal against the face of a user, such as shown in FIG. 15B.

Figure 16A:
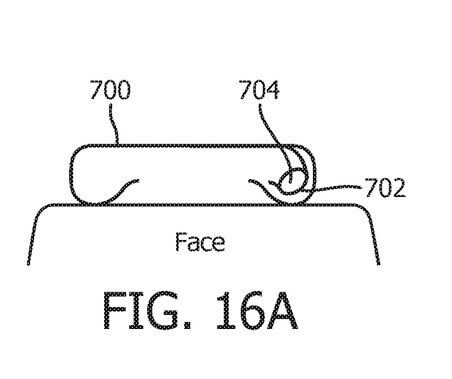
FIGS. 16A and 16B are schematic sectional views of a mask in accordance with one example embodiment of the present invention taken from a similar position as the sectional views of FIGS. 11A and 11B.
Figure 16B:
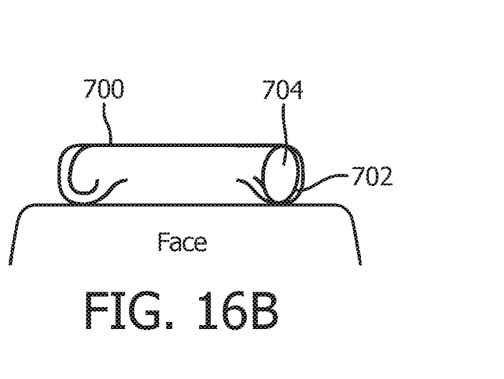

FIGS. 16A and 16B show schematic section views, similar to those of FIGS. 11A, 11B, 13A, 13B, 14A, 14B 15A and 15B, of a mask 700 in accordance with an example embodiment of the present invention disposed on the face of a user. Referring to FIG. 16A, mask 700 includes a support flap 702 having a thin-walled pouch 704 formed therein. As shown in FIG. 16A, when no flow or an insufficient flow of treatment gas is provided pouch 704 is deflated, thus causing one or more air gaps. Conversely, when a sufficient flow of treatment gas is provided, thin-walled pouch 704 is inflated, thus causing mask 700 to tightly seal against the face of a user, such as shown in FIG. 16B.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A mask for use in a patient interface device for delivering a flow of breathing gas to an airway of a patient, the mask comprising:
   a first portion formed from a pliable material, the first portion having at least one aperture defined therethrough;
   a cavity defined at least in-part by the first portion and accessible via a port defined in the mask, the cavity being structured to receive the flow of breathing gas provided to the port and to communicate the flow to the airway of the patient; and
   a member formed from another pliable material, the member disposed in the cavity and coupled to the first portion, the member movable from:
      a first position in which the member is directly sealingly engaged with the pliable material of the first portion about a periphery of the at least one aperture and is structured to prevent passage of the breathing gas from the cavity through the at least one aperture, and
      a second position in which at least a portion of the member is spaced from the periphery of the at least one aperture and is structured to allow passage of a gas external to the cavity into the cavity through the at least one aperture,
   wherein the member comprises a sheet-like pliable member,
   wherein the at least one aperture comprises a plurality of apertures, and
   wherein the sheet-like pliable member includes:
   a first portion movable from a first position in which the first portion is sealingly engaged about a periphery of a first aperture of the plurality of apertures thus preventing passage of a fluid through the first aperture and a second position in which at least a portion of the first portion is spaced from the periphery of the first aperture such that the fluid is able to pass through the first aperture; and
   a second portion movable independently from a first position in which the second portion is sealingly engaged about a periphery of a second aperture of the plurality of apertures thus preventing passage of the fluid through the second aperture and a second position in which at least a portion of the second portion is spaced from the periphery of the second aperture such that the fluid is able to pass through the second aperture.

2. The mask of claim 1, wherein the sheet-like pliable member is of a generally constant thickness.

3. The mask of claim 1, wherein the sheet-like pliable member has a thickness of about 0.001 inches.

4. The mask of claim 1, wherein the cavity is readily deformable between a first positioning wherein the cavity defines a first volume and a second positioning wherein the cavity defines a second volume which is less than 60% of the first volume.

5. An airway pressure support system comprising:
a pressure/flow generator structured to produce a flow of breathing gas;
a delivery conduit structured to communicate the flow of breathing gas; and
a patient interface device having a mask comprising:
   a first portion formed from a pliable material, the first portion having at least one aperture defined therethrough;
   a cavity defined at least in-part by the first portion and accessible via a port defined in the mask, the cavity being structured to receive the flow of breathing gas communicated by the delivery conduit from the pressure/flow generator to the port and to communicate the flow to an airway of a patient; and
   a member formed from another pliable material, the member disposed in the cavity and coupled to the first portion, the member movable from:
      a first position in which the member is directly sealingly engaged with the pliable material of the first portion about a periphery of the at least one aperture and is structured to prevent passage of the breathing gas from the cavity through the at least one aperture, and
      a second position in which at least a portion of the member is spaced from the periphery of the at least one aperture and is structured to allow passage of a gas external to the cavity into the cavity through the at least one aperture,
wherein the member comprises a sheet-like pliable member,
wherein the at least one aperture comprises a plurality of apertures, and
wherein the sheet-like pliable member includes:
   a first portion movable from a first position in which the first portion is sealingly engaged about a periphery of a first aperture of the plurality of apertures thus preventing passage of a fluid through the first aperture and a second position in which at least a portion of the first portion is spaced from the periphery of the first aperture such that the fluid is able to pass through the first aperture; and
   a second portion movable independently from a first position in which the second portion is sealingly engaged about a periphery of a second aperture of the plurality of apertures thus preventing passage of the fluid through the second aperture and a second position in which at least a portion of the second portion is spaced from the periphery of the second aperture such that the fluid is able to pass through the second aperture.

6. The airway pressure support system of claim 5, wherein the sheet-like pliable member is of a generally constant thickness.

7. The airway pressure support system of claim 5, wherein the sheet-like pliable member has a thickness of about 0.001 inches.

8. The airway pressure support system of claim 5, wherein the cavity is readily deformable between a first positioning wherein the cavity defines a first volume and a second positioning wherein the cavity defines a second volume which is less than 60% of the first volume.

* * * * *